(12) United States Patent
Altshuler et al.

(10) Patent No.: US 7,276,058 B2
(45) Date of Patent: Oct. 2, 2007

(54) METHOD AND APPARATUS FOR TREATMENT OF CUTANEOUS AND SUBCUTANEOUS CONDITIONS

(75) Inventors: Gregory B. Altshuler, Wilmington, MA (US); Ilya Yaroslavsky, Wilmington, MA (US); Andre Viacheslavovitch Belikov, St. Petersburg (RU); Konstantin Prikhodko, Viborg (RU)

(73) Assignee: Palomar Medical Technologies, Inc., Burlington, MA (US)

( * ) Notice: Subject to any disclaimer, the term of this patent is extended or adjusted under 35 U.S.C. 154(b) by 198 days.

(21) Appl. No.: 10/465,757

(22) Filed: Jun. 19, 2003

(65) Prior Publication Data
US 2004/0073079 A1    Apr. 15, 2004

Related U.S. Application Data

(60) Provisional application No. 60/389,871, filed on Jun. 19, 2002.

(51) Int. Cl.
*A61B 18/18* (2006.01)

(52) U.S. Cl. .............. 606/9; 606/10; 606/11; 606/22; 607/88; 128/898

(58) Field of Classification Search .......... 606/3, 606/9–12, 20, 22–29; 607/88, 89, 91, 96, 607/100, 104; 128/898
See application file for complete search history.

(56) References Cited

U.S. PATENT DOCUMENTS

| | | | |
|---|---|---|---|
| 1,706,161 A | 3/1929 | Hollnagel | |
| 2,472,385 A | 6/1949 | Rollman | |
| 3,327,712 A | 6/1967 | Kaufman et al. | |
| 3,486,070 A | 12/1969 | Engel | |
| 3,527,932 A | 9/1970 | Thomas | |
| 3,538,919 A | 11/1970 | Meyer | |
| 3,597,652 A | 8/1971 | Gates, Jr. | |
| 3,622,743 A | 11/1971 | Muncheryan | |

(Continued)

FOREIGN PATENT DOCUMENTS

DE    9102407    7/1991

(Continued)

OTHER PUBLICATIONS

Altea Therapeutics—Medicines Made Better (single page website print-out).

(Continued)

*Primary Examiner*—A. Farah
(74) *Attorney, Agent, or Firm*—Thomas J. Engellenner; Deborah A. Miller; Nutter McClennen & Fish LLP (57) ABSTRACT

The present invention provides method and apparatus for treating tissue in a region at depth while protecting non-targeted tissue by cyclically applying cooling to the patients skin, and preferably to the region, and by applying radiation to the patient's skin above the region to selectively heat tissue during and/or after cooling is applied. At least one of cooling and radiation my be applied by successivly passing a continuous output applicator over the patient's skin. Treatment may also be enhanced by applying mechanical, acoustic or electrical stimulation to the region.

48 Claims, 6 Drawing Sheets

U.S. PATENT DOCUMENTS

| | | |
|---|---|---|
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,900,034 A | 8/1975 | Katz et al. |
| 4,233,493 A | 11/1980 | Nath |
| 4,273,109 A | 6/1981 | Enderby |
| 4,275,335 A | 6/1981 | Ishida |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A | 9/1985 | Nath et al. |
| 4,561,440 A | 12/1985 | Kubo et al. |
| 4,591,762 A | 5/1986 | Nakamura |
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,905,690 A | 3/1990 | Ohshiro et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,066,293 A | 11/1991 | Furumoto |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,287,380 A | 2/1994 | Hsia |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,342,358 A | 8/1994 | Daikuzono et al. |
| 5,344,418 A * | 9/1994 | Ghaffari ............... 606/9 |
| 5,344,434 A | 9/1994 | Talmore |
| 5,348,551 A | 9/1994 | Spears et al. |
| 5,350,376 A | 9/1994 | Brown |
| 5,358,503 A | 10/1994 | Bertwell et al. |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,458,140 A | 10/1995 | Eppstein et al. |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,531,740 A | 7/1996 | Black |
| 5,549,660 A | 8/1996 | Mendes et al. |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,148 A | 8/1997 | Neuberger et al. |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,722,397 A | 3/1998 | Eppstein |
| 5,735,844 A | 4/1998 | Anderson et al. |
| 5,735,884 A | 4/1998 | Thompson et al. |
| 5,742,392 A | 4/1998 | Anderson et al. |
| 5,743,901 A | 4/1998 | Grove et al. |
| 5,746,735 A | 5/1998 | Furumoto et al. |
| 5,755,751 A | 5/1998 | Eckhouse |
| 5,759,200 A | 6/1998 | Azar |
| 5,769,076 A | 6/1998 | Mackawa et al. |
| 5,782,249 A | 7/1998 | Weber et al. |
| 5,810,801 A | 9/1998 | Anderson et al. |
| 5,814,008 A | 9/1998 | Chen et al. |
| 5,814,040 A * | 9/1998 | Nelson et al. ............ 606/9 |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A * | 11/1998 | Muller ............... 606/9 |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,913,883 A | 6/1999 | Alexander et al. |
| 5,916,211 A | 6/1999 | Quon et al. |
| 5,944,748 A | 8/1999 | Mager et al. |
| 5,948,011 A * | 9/1999 | Knowlton ............ 607/101 |
| 5,949,222 A | 9/1999 | Buono |
| 5,954,710 A | 9/1999 | Paolini et al. |
| 5,955,490 A | 9/1999 | Kennedy et al. |
| 5,964,749 A | 10/1999 | Eckhouse et al. |

| Patent | Date | Inventor |
|---|---|---|
| 5,968,033 A | 10/1999 | Fuller et al. |
| 5,968,034 A | 10/1999 | Fullmer et al. |
| 5,976,123 A | 11/1999 | Baumgardner et al. |
| 5,977,723 A | 11/1999 | Yoon |
| 5,984,915 A | 11/1999 | Loeb et al. |
| 6,015,404 A | 1/2000 | Altshuler et al. |
| 6,022,316 A | 2/2000 | Eppstein et al. |
| 6,026,828 A | 2/2000 | Altshuler |
| 6,027,495 A | 2/2000 | Miller |
| 6,030,399 A | 2/2000 | Ignotz et al. |
| 6,032,071 A | 2/2000 | Binder |
| RE36,634 E | 3/2000 | Ghaffari |
| 6,036,684 A | 3/2000 | Tankovich et al. |
| 6,050,990 A | 4/2000 | Tankovich et al. |
| D424,197 S | 5/2000 | Sydlowski et al. |
| 6,056,738 A | 5/2000 | Marchitto et al. |
| 6,059,820 A * | 5/2000 | Baronov .................. 607/89 |
| 6,074,382 A | 6/2000 | Asah et al. |
| 6,080,146 A | 6/2000 | Altshuler et al. |
| 6,086,580 A | 7/2000 | Mordon et al. |
| 6,096,029 A | 8/2000 | O'Donnell, Jr. |
| 6,096,209 A | 8/2000 | O'Brien et al. |
| 6,104,959 A * | 8/2000 | Spertell .................. 607/101 |
| 6,117,129 A | 9/2000 | Mukai |
| 6,120,497 A | 9/2000 | Anderson |
| 6,142,939 A | 11/2000 | Eppstein et al. |
| 6,149,644 A | 11/2000 | Xie |
| 6,162,055 A | 12/2000 | Montgomery et al. |
| 6,162,211 A | 12/2000 | Tankovich et al. |
| 6,162,212 A | 12/2000 | Kreindel et al. |
| 6,173,202 B1 | 1/2001 | Eppstein et al. |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,197,020 B1 | 3/2001 | O'Donnell |
| 6,210,425 B1 | 4/2001 | Chen |
| 6,214,034 B1 | 4/2001 | Azar |
| 6,228,075 B1 | 5/2001 | Furumoto |
| 6,229,831 B1 | 5/2001 | Nightingale et al. |
| 6,235,016 B1 | 5/2001 | Stewart |
| 6,236,891 B1 | 5/2001 | Ingel et al. |
| 6,245,093 B1 | 6/2001 | Li et al. |
| 6,263,233 B1 | 7/2001 | Zavislan et al. |
| 6,264,649 B1 | 7/2001 | Whitcroft et al. |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,290,713 B1 | 9/2001 | Russell |
| 6,306,130 B1 | 10/2001 | Anderson et al. |
| 6,319,274 B1 | 11/2001 | Shadduck |
| 6,340,495 B1 | 1/2002 | Sumian et al. |
| 6,343,933 B1 | 2/2002 | Montgomery et al. |
| 6,350,276 B1 * | 2/2002 | Knowlton .................. 607/104 |
| 6,354,370 B1 | 3/2002 | Miller et al. |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,406,474 B1 | 6/2002 | Neuberger et al. |
| 6,424,852 B1 | 7/2002 | Zavislan |
| 6,425,912 B1 | 7/2002 | Knowlton |
| 6,436,094 B1 | 8/2002 | Reuter |
| 6,461,296 B1 | 10/2002 | Desai |
| 6,471,712 B2 | 10/2002 | Burres |
| 6,471,716 B1 | 10/2002 | Pecukonis |
| 6,475,211 B2 | 11/2002 | Chess et al. |
| 6,494,900 B1 | 12/2002 | Salansky et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,530,915 B1 | 3/2003 | Eppstein et al. |
| 6,537,270 B1 | 3/2003 | Elbrecht et al. |
| 6,558,372 B1 | 5/2003 | Altshuler |
| 6,569,155 B1 | 5/2003 | Connors et al. |
| 6,572,637 B1 | 6/2003 | Yamazaki et al. |
| 6,602,245 B1 | 8/2003 | Thiberg |
| 6,605,080 B1 | 8/2003 | Altshuler et al. |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,600 B1 | 11/2003 | Kohler |
| 6,648,904 B2 | 11/2003 | Altshuler et al. |
| 6,653,618 B2 | 11/2003 | Zenzie |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,676,654 B1 | 1/2004 | Balle-Petersen et al. |
| 6,679,837 B2 | 1/2004 | Daikuzono |
| 6,685,699 B1 | 2/2004 | Eppstein et al. |
| 6,689,124 B1 | 2/2004 | Thiberg |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,770,069 B1 | 8/2004 | Hobart et al. |
| 6,790,205 B1 | 9/2004 | Yamazaki et al. |
| 6,808,532 B2 | 10/2004 | Andersen et al. |
| RE38,670 E | 12/2004 | Asah et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 2001/0041886 A1 | 11/2001 | Durkin et al. |
| 2002/0005475 A1 | 1/2002 | Zenzie |
| 2002/0026225 A1 | 2/2002 | Segal |
| 2002/0091377 A1 | 7/2002 | Anderson |
| 2002/0128635 A1 | 9/2002 | Altshuler et al. |
| 2002/0161357 A1 | 10/2002 | Anderson |
| 2002/0173780 A1 | 11/2002 | Altshuler et al. |
| 2003/0004499 A1 | 1/2003 | McDaniel |
| 2003/0023283 A1 | 1/2003 | McDaniel |
| 2003/0032900 A1 | 2/2003 | Ella |
| 2003/0032950 A1 | 2/2003 | Altshuler et al. |
| 2003/0036680 A1 | 2/2003 | Black |
| 2003/0055414 A1 | 3/2003 | Altshuler et al. |
| 2003/0057875 A1 | 3/2003 | Inochkin et al. |
| 2003/0065314 A1 | 4/2003 | Altshuler et al. |
| 2003/0100936 A1 | 5/2003 | Altshuler et al. |
| 2003/0109787 A1 | 6/2003 | Black |
| 2003/0109860 A1 | 6/2003 | Black |
| 2003/0129154 A1 | 7/2003 | McDaniel |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0024388 A1 | 2/2004 | Altshuler |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0093042 A1 | 5/2004 | Altshuler et al. |
| 2004/0133251 A1 | 7/2004 | Altshuler et al. |

| | | | |
|---|---|---|---|
| 2004/0143920 A1 | 7/2004 | Nanda | |
| 2004/0147984 A1 | 7/2004 | Altshuler et al. | |
| 2004/0162549 A1 | 8/2004 | Altshuler et al. | |
| 2004/0162596 A1 | 8/2004 | Altshuler et al. | |
| 2004/0191729 A1 | 9/2004 | Altshuler et al. | |
| 2004/0193235 A1 | 9/2004 | Altshuler et al. | |
| 2004/0193236 A1 | 9/2004 | Altshuler et al. | |
| 2004/0199227 A1 | 10/2004 | Altshuler et al. | |
| 2004/0204745 A1 | 10/2004 | Altshuler et al. | |
| 2004/0210276 A1 | 10/2004 | Altshuler et al. | |
| 2004/0214132 A1 | 10/2004 | Altshuler | |
| 2004/0225339 A1 | 11/2004 | Yaroslavsky et al. | |
| 2004/0230258 A1 | 11/2004 | Altshuler et al. | |
| 2005/0038418 A1 | 2/2005 | Altshuler et al. | |
| 2005/0049582 A1 | 3/2005 | DeBenedictis et al. | |
| 2005/0049658 A1 | 3/2005 | Connors et al. | |
| 2005/0107849 A1 | 5/2005 | Altshuler et al. | |

FOREIGN PATENT DOCUMENTS

| | | |
|---|---|---|
| EP | 0743029 | 11/1996 |
| EP | 0884066 | 12/1998 |
| EP | 0885629 | 12/1998 |
| EP | 1138349 | 10/2001 |
| EP | 1147785 | 10/2001 |
| EP | 1226787 | 7/2002 |
| EP | 1 457 234 A2 | 9/2004 |
| GB | 1546625 | 5/1979 |
| GB | 2356570 | 5/2001 |
| GB | 2368020 | 4/2002 |
| GB | 2390021 | 12/2003 |
| GB | 2397528 | 7/2004 |
| JP | 2001145520 | 5/2001 |
| JP | 2003192809 | 2/2005 |
| WO | WO88/04592 | 6/1988 |
| WO | WO91/13652 | 9/1991 |
| WO | WO96/36396 | 11/1996 |
| WO | WO96/41579 | 12/1996 |
| WO | WO98/58595 | 12/1998 |
| WO | WO99/17666 | 4/1999 |
| WO | WO99/17667 | 4/1999 |
| WO | WO99/27863 | 6/1999 |
| WO | WO 00/02491 | 1/2000 |
| WO | WO 00/32272 | 6/2000 |
| WO | WO 00/40266 | 7/2000 |
| WO | WO 00/43070 | 7/2000 |
| WO | WO 00/44294 | 8/2000 |
| WO | WO 00/64537 | 11/2000 |
| WO | WO 00/74583 | 12/2000 |
| WO | WO 01/26573 | 4/2001 |
| WO | WO 01/54770 | 8/2001 |
| WO | WO 01/68185 | 9/2001 |
| WO | WO 01/78830 | 10/2001 |
| WO | WO 02/069825 | 9/2002 |
| WO | WO 2004/073537 | 9/2004 |
| WO | WO 2004/084752 | 10/2004 |
| WO | WO 2004/086947 A2 | 10/2004 |
| WO | WO 2005/007003 A1 | 1/2005 |

OTHER PUBLICATIONS

Derma Chiller advertisement (2 pages) from Paradigm Trex.
Doukas et al., "Transdermal Drug Delivery With a Pressure Wave," Advanced Drug Delivery Reviews 56 (2004), pp. 559-579.
E.J. Fiskerstrand et al., "Hair Removal With Long Pulsed Diode Lasers: A Comparison Between Two Systems With Different Pulse Structures," Lasers in Surgery and Medicine, vol. 32, pp. 399-404, 2003.
Ohshiro et al., "The Ruby and Argon Lasers in the Treatment of the Naevi," Annals Academy of Medicine, Apr. 1983, vol. 12, No. 2, pp. 388-395.
Riggle et al., "Laser Effects On Normal And Tumor Tissue," Laser Applications in Medicine and Biology, vol. 1, M.L. Wolbarsht, editor, Plenum Press, publishers, Chapter 3, pp. 35-65, 1971.
Sumian, C.C. et al., "A Preliminary Clinical And Histopathological Study Of Laser Skin Resurfacing Using A Frequency-Doubled Nd:YAG Laser After Application of Chromofilm®," Journal of Cutaneous Laser Therapy, vol. 1, pp. 159-166, 1999.
Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.

* cited by examiner

METHOD AND APPARATUS FOR TREATMENT OF CUTANEOUS AND SUBCUTANEOUS CONDITIONS

CROSS-REFERENCE TO RELATED APPLICATION

This invention claims the benefit of now abandoned U.S. Provisional Patent Application Ser. No. 60/389,871, filed Jun. 19, 2002, entitled "Method and Apparatus for Subdermal Heating," by G. Altshuler, et al., incorporated herein by reference in its entirety.

BACKGROUND

1. Field of the Invention

This invention relates to methods and apparatus for the photothermal treatment of tissue and, more particularly, to methods and apparatus for treating cutaneous and subcutaneous conditions at depth.

2. Description of the Related Art

The benefits of being able to raise and/or lower the temperature in a selected region of tissue for various therapeutic and cosmetic purposes has been known for some time. For instance, heated pads or plates or various forms of electromagnetic radiation, including visible, infrared and microwave radiation, electricity, and ultrasound have previously been used for heating subdermal muscles, ligaments, bones and the like to, for example, increase blood flow, to otherwise promote the healing of various injuries and other damage, and for various therapeutic purposes, such as frostbite or hyperthermia treatment, treatment of poor blood circulation, physical therapy, stimulation of collagen, cellulite treatment, adrenergic stimulation, wound healing, psoriasis treatment, body reshaping, non-invasive wrinkle removal, etc. The heating of tissues has also been utilized as a potential treatment for removing cancers or other undesired growths, infections and the like. Heating may be applied over a small localized area, over a larger area, for example to the hands or feet, or over larger regions of tissue, including the entire body.

Since most of the techniques described above involve applying energy to tissue at depth through the patient's skin surface, peak temperature generally occurs at or near the patient's skin surface and decrease, sometimes significantly, with depth. Further, while microwaves or ultrasonic and other acoustic radiation have been used in the past, such radiation has had limited use because, particularly for microwaves, they may be potentially mutagenic, may potentially otherwise result in cell or systemic damage and, particularly for acoustic sources, are relatively expensive. They may also not be practical for large-area treatment.

While optical and near infrared (NIR) radiation (collectively referred to hereinafter as "optical radiation" is generally both less expensive and, being non-mutagenic, safer than microwaves radiation, the use of optical radiation has heretofore not been considered suitable for most applications involving heating of tissue at depth, the term "tissue at depth" as used herein meaning tissue at the border zone of the dermis and hypodermis or subcutaneous region, some of which tissue may be in the lower dermis, mostly at a depth deeper than 1 mm, and tissue below this border zone to a depth of up to about 50 mm The reason why this radiation has not been considered suitable is because such radiation is both highly scattered and highly absorbed in surface layers of tissue, precluding significant portions of such radiation from reaching the tissue regions at depth to cause heating thereof. In view of the energy losses due to scattering and absorption, substantial optical (including NIR) energy must be applied in order for enough such energy to reach a region of tissues at depth to have a desired effect. However, such high energy can cause damage to the surface layers of tissue and pain/discomfort to the patient, making it difficult to achieve desired photothermal treatments in tissue regions at depth. For these reasons, optical radiation has heretofore had at most limited value for therapeutic and cosmetic treatments on tissue at depth.

While heating or cooling of tissue at depth alone has proved useful for many treatments, the combination of heating and cooling applied intermittently to the skin surface (known as contrast therapy) is also known and has been suggested for skin improvement, pain relief, inflammation reduction, and healing of injury. Of particular importance is the application of these techniques for reducing subcutaneous fat deposits and treating cellulite (gynoid lipodystrophy). However, use of cooling or heating, either alone or in combination for treatment of conditions at depth, for example for skin improvement, cellulite improvement, fat reduction, and treatment of other conditions has been limited by the body's pain/discomfort tolerance and by the damage limits of treated organs and adjacent, especially cutaneous, tissue that need to be kept intact.

A need therefore exists for improved method and apparatus for photothermal treatment of tissue regions at depth, and in particular for treatment of deep dermis and subcutaneous regions of tissue, which treatments provide improved treatment results, while both reducing patient pain and discomfort and protecting adjacent and other non-treatment tissue from damage.

SUMMARY OF THE INVENTION

In accordance with the above, this invention provides a method and apparatus for treating at least a selected target region at depth, as this term has previously been defined, of a patient's body, while protecting non-targeted tissue by utilizing a suitable mechanism to cool the patient's skin surface to a temperature below normal body temperature for a selected duration; utilizing a suitable mechanism to selectively apply radiation to the patient's skin above said region before, during and/or after cooling; and repeating the cooling and radiation application for a selected number of cycles, the temperature to which the patient's skin is cooled and the duration of cooling being sufficient to cool the treatment region to a selected temperature below normal body temperature during at least cooling portions of cycles. The cooling duration should be at least about 10 seconds, normally being between approximately 10 seconds and 20 minutes. Where radiation is applied after cooling, the radiation may be applied for approximately one second to 4 minutes. The cooling may be performed continuously while the radiation is applied at intervals during the cooling. Where the selected region is subcutaneous fat, the selected temperature should be low enough to result in at least a selective phase change of at least a portion of the fat. In this case, the radiation should be of sufficient power and duration and of appropriate wavelength to heat the treatment region to at least a temperature where the phase of the fat cells is altered. Alternatively, the radiation may be of sufficient power and duration and of appropriate wavelength to heat the treatment region to a temperature where at least one of the biophysical and biochemical characteristics of cells in the region is altered. Alternatively, the radiation should be of sufficient power and duration and of appropriate wavelength to heat tissue above the treatment region to protect the tissue, but not to significantly heat the treatment region. For another embodiment, the treatment involves cycling cooling and heating of the treatment region, radiation being applied after cooling and the radiation being of sufficient power and duration and of appropriate wavelength to heat the region to an appropriate temperature to effect the treatment. For some embodiments, a selected condition of the patient is detected and utilized to control at least a portion of the operation. Stimulation of the selected region may also be utilized before, during and/or after at least one of the operations, such stimulation being generally at least one of mechanical, acoustic and electrical. The period and/or phase of the treatment cycles may be correlated with a sub-circadian rhythm of the patient.

For some embodiments, the radiation is from a continuous wave source and cooling is also performed from a substantially continuously operating source. For these embodiments, cooling and radiation application are each performed by passing an applicator outputting the appropriate source over the patient's overlying the treatment region at a selected rate. The same applicator may be used to perform both cooling ad radiation application for these embodiments and the applicator my perform both operations during the same pass or separate passes.

In accordance with another aspect of the invention, radiation is selectively delivered to the patients body above the selected region to heat the region; patient tissue above the selected region is concurrently cooled to a temperature below that of the selected region; and the region is cooled to a temperature below normal body temperature before and/or after the heating of the region.

In accordance with still another aspect of the invention, treatment is performed by cyclically applying radiation and cooling to the surface of the patient's skin above the selected region through at least one applicator providing substantially continuous cooling/radiation output, which applicator is passed over the patient's skin over the region multiple times for each cooling/radiation cycle.

Other advantages, novel features, and objects of the invention will become apparent from the following detailed description of the invention when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

Non-limiting embodiments of the present invention will be described by way of example with reference to the accompanying drawings in which:

FIG. 8a is a cut-away side view of an optical head suitable use in practicing the teachings of the invention;

FIG. 8b is an enlarged cut-away side view of a portion of the head shown in FIG. 8a;

DETAILED DESCRIPTION

Applications in which the invention may be useful include the treatment of various pathological and cosmetic conditions, particularly skin rejuvenation, wrinkle removal, skin tightening and lifting, reduction of odor production, hair growth control, acne treatment, cellulite and subcutaneous fat treatment, physical therapy, muscle and skeletal treatments, including treatment of spinal cord problems, and treatment of cumulative trauma disorders (CTD's) such as carpel tunnel syndrome (CTS), tendonitis and bursitis, fibromyalgia, lymphedema and cancer therapy.

The application of thermal energy, either heating or cooling, to tissue may also be used, for example, in physical therapy treatments, such as to enhance or accelerate wound healing or relieve pain. Beneficial effects may include a decrease in joint stiffness, an increase in joint extensibility of collagenous structures such as tendons and scar tissue, pain relief, blood-flow changes, or a decrease in muscle spasm and increase in muscle tone. As another example, large protein molecules may have high absorption coefficients, and the heating of protein-rich collagenous tissues may contribute to healing. A wide variety of conditions may be treated using this invention, for example, but not limited to, strained tendons, tenosynovitis, torn ligaments, tendonitis, bursitis, torn joint capsules, or torn muscles. Thermal treatment can be effective on highly metabolic organs such as sebaceous gland, sweat glands and hair follicles. Other processes may be activated or deactivated within tissue during cooling or heating. Mechanical or electrical stimulation, such as massage, may also be used in conjunction with cooling or heating to achieve benefits greater then can be achieved by either alone. Positive and negative pressure may also be applied to the skin surface above the treatment region to facilitate the treatment.

In certain embodiments, the present invention may be used for non-invasive or nondestructive reduction of localized fat deposits. For example, the invention may be used to heat fat or adipose cells past their damage temperature, causing cell damage and/or necrosis. Alternatively, the treated cells may undergo apoptosis, resulting in cell death. The dead cells may then be removed or resorbed into the body, for example, by the body's phagocytic or lymphatic systems. Fat reduction may also be achieved by heating fat or adipose cells to an elevated temperature, but below the damage temperature. For example, the fat cells may be heated to a temperature of between about 41° C. and about 45° C. Under these conditions, applying heat to subcutaneous fat may activate lipases or metabolize lipids contained within the adipose tissue found within the subcutaneous fat layer, or blood flow may increase to the heated area. Additionally, "lipolysis," or the process of breaking down fat in the body, may be regulated by enzymes sensitive to temperature, such as HSL ("hormone-sensitive lipase"). Thus, elevating the temperature of the adipose cells may increase the lipolysis rate, and thus contribute to a reduction in subdermal fat in the area being treated. This temperature can be below the temperature for vascular/lymph damage so damaged fatty cells and fatty acids can be easily removed from the treatment region. Additionally, application of the present invention may be used in combination with other fat-reduction techniques, such as medication, exercise, or adrenergic stimulation The invention also includes cooling of the fat tissue to a temperature below normal body temperature, and preferably below the phase transition temperature of at least some fraction of the lipid content of fatty cells, which temperature is substantially higher then the freezing temperature of water-containing tissue, preceded or preferably followed by heating the fat to a temperature below its damage threshold. Triglycerides (which constitute the largest fraction of lipids in human fatty tissue) undergo a series of phase transitions when their temperature changes from normal body temperature to either a lower or higher temperature. Specifically, several crystalline forms can exist. These forms are (in the order of increasing stability): α, β', and β. The latter crystals are also significantly larger in size (as needle of a dozen microns length). Crystal formation can be the reason for fatty cell dysfunction and shrinkage resulting from mechanical stress on cell structure and/or destruction of cell metabolism. β crystal formation can the primer mechanism for fatty cell treatment. When triglycerides are cooled from normal body temperature, formation of α-crystals takes place. In order to produce more stable forms, β' first and β second, reverse heating of the crystallized triglycerides is required. Further heating leads to complete melting of all crystalline forms.

Therefore, the following process is suggested to initiate formation of β-crystals in adipose cells. First, the fatty tissue is cooled to a lower-than-normal temperature $T_\alpha$ (in the range between 0 and 37 C). This results in α-crystals being formed. Then, the tissue is heated back to a temperature $T_\beta > T_\alpha$ but below 37 C, causing formation of β'- and β-crystals. Finally, the tissue can be heated to even higher temperature in order to melt the crystals, and the process can be repeated for a selected number of cycles. The expected final result is dystrophy and decrease in volume of fatty tissue. This process takes place for all temperature range 0-37 but for lower $T_\alpha$ this process is more effective. Thermal activation of lymph systems in subcutaneous fat can also be used to treat cellulite by removing proteins from extra cell spaces.

Figure 1:
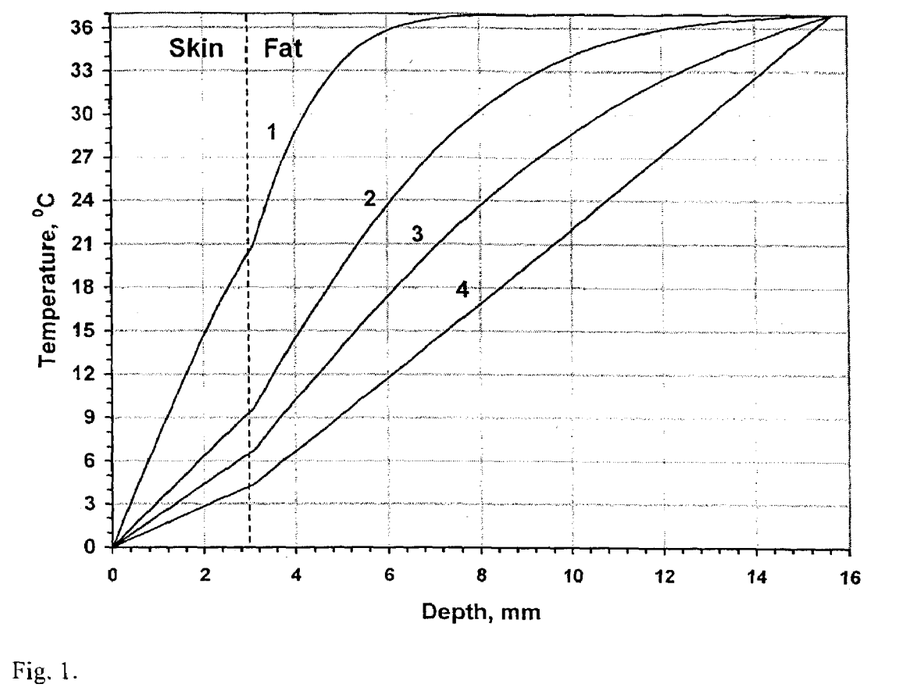
FIG. 1 is a diagram illustrating the temperature/depth profile of the skin and subcutis at various times after the onset of surface cooling.
Figure 2:
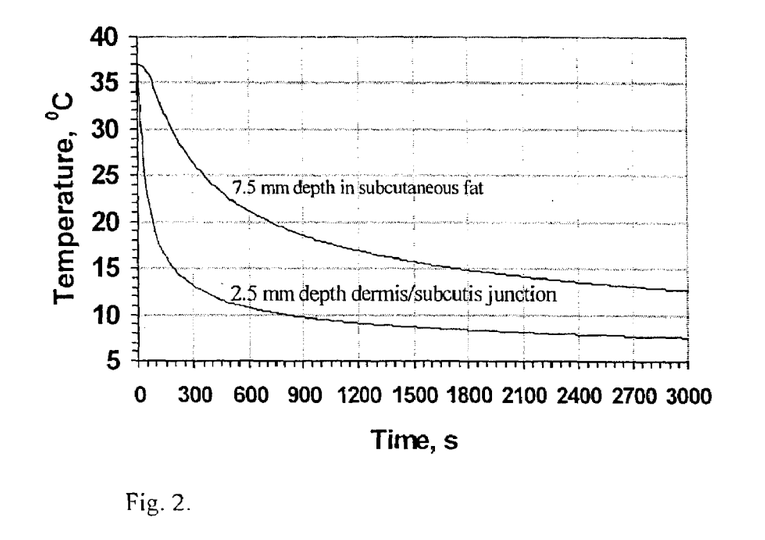
FIG. 2 is a diagram illustrating temperature in the human body as a function of cooling time for various depths.

Application of a cooling panel (agent or device) to the skin surface causes the temperature of skin and the subcutaneous region or subcutis to drop gradually, as illustrated by FIG. 1. In FIG. 1, curve (1) is after one minute, curve (2) after five minutes, curve (3) after ten minutes, and curve (4) after thirty minutes of application of a cooling panel to the skin surface. The depth of the skin/fat or dermis/subcutaneous boundary, shown at 3 mm in FIG. 1, will vary depending on a number of factors including the patient and the portion of the patient's body being treated. The rate of cooling and the final temperature depend on the depth of the target and the temperature of the skin surface. FIG. 2 shows the calculated temperature dynamics of the dermis-subcutis junction at 2.5 mm depth and in subcutaneous fat at 7.5 mm depth resulting from a constant surface temperature of 0° C. Substantial cooling of targets in the skin can be achieved in the time range between 10 s and 300 s. Deeper targets in subcutaneous fat need cooling times in the range between 2 min and 30 min. Cooling time can be shortened by simultaneously coupling into the skin pressure or acoustic waves or by intensive massage of cooled skin. The acoustic waves or mechanical massage can increase the heat conductivity of the skin and subcutaneous fat by forced convection of inter-cellular water.

Depending on the surface temperature and the duration of application, a number of processes can be initiated in the fatty and other tissues, including, but not limited to:

Phase transitions in lipids;

Changes in regulatory functions of the adipocyte. In particular, lower temperatures may suppress activity of Alpha2 receptors, which inhibit adenylate cyclase and cyclic AMP through Gi protein and thus decrease lypolisis rate. This can lead to long-term atrophy of fatty cells after cold exposure;

Increase of ion concentration in intracellular water. Such an increase is caused by partial binding of free water in the course of fat crystallization. Transition of water into bound state has been demonstrated spectroscopically. As a result, concentration of ions in the remaining free water increases. Once the ion concentration exceeds a critical level, irreversible damage to the vital mechanisms of the cell can occur;

Water crystallization in tissues;

Induction of apoptosis;

Tissue necrosis;

Stimulation of thermogenesis

Remodeling of vascular and lymph vessels;

Temporal or permanent dysfunction of follicles, sebaceous and sweat glands.

Figure 3:
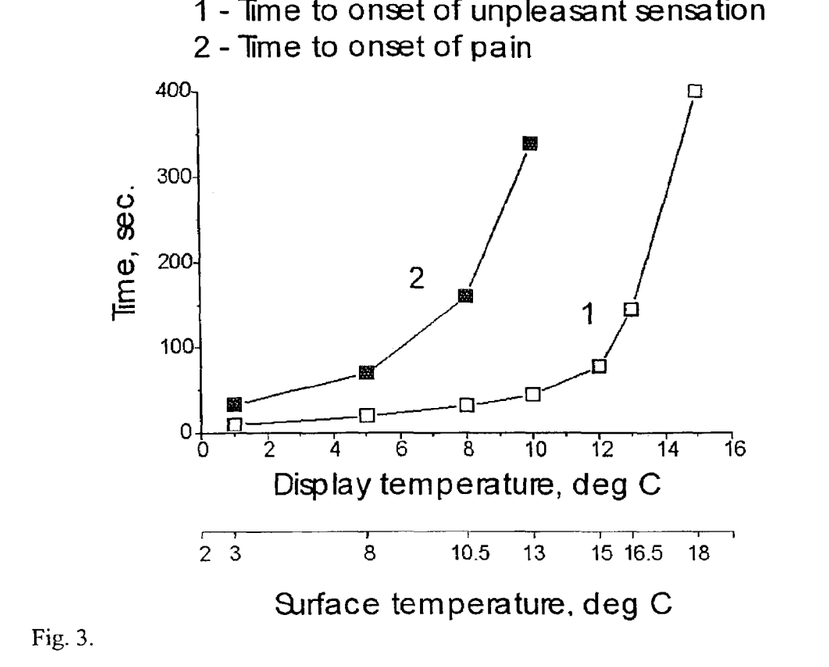
FIG. 3 is a diagram illustrating the onset time of patient discomfort and of patient pain as a function of skin surface temperature.

In practical use, cold exposure time is limited by the onset of unpleasant and, subsequently, painful sensations. FIG. 3 illustrates the dependence of these onset times on the temperature at the skin surface. As a result, the practical application time may be insufficient to achieve a desired therapeutic effect.

Thermal cycling, comprised of cooling and heating phases, may be used to eliminate both the pain/discomfort and unwanted tissue damage outside the target region. It should be emphasized that, although methods and devices alternating skin surface temperature between hot and cold have previously been proposed, the thermal inertia of tissue prevents rapid propagation of a heat front from the skin surface to a desired treatment depth (or vice versa).

This invention therefore uses deep-penetrating electromagnetic or acoustic radiation to create distributed heat sources within tissue. This allows increasing the treatment time substantially and achieving acceptable therapeutic effect, while maintaining both complete non-invasiveness of the procedure and patient comfort.

Beneficial effects of thermal cycling are not limited to treatment of fatty tissue. Thermal cycling initiates a number of biophysical and biochemical responses at molecular, cellular, tissue, and organ levels, including (but not limited to):

- modulation of cell membrane's permeability and, therefore, inter-membrane transport and exchange between intra- and interstitial compartments;
- induction of thermo-mechanical stress in the target (for example, malignant) cells, leading to cell death through either necrosis or apoptosis;
- changes in elasticity and permeability of vessel walls;
- changes in blood rheology;
- stimulation of tissue regeneration, including new collagen generation in skin and subcutis;
- changes of toxin structure in the interstitial fluid making them amenable for easy removal by lymphatic systems.

As a result, thermal cycling can be used for treatment of a wide range of conditions, involving skin, subcutaneous fat, connective tissues, blood and lymph vasculature, muscles, bones, and other internal organs.

Figure 4:
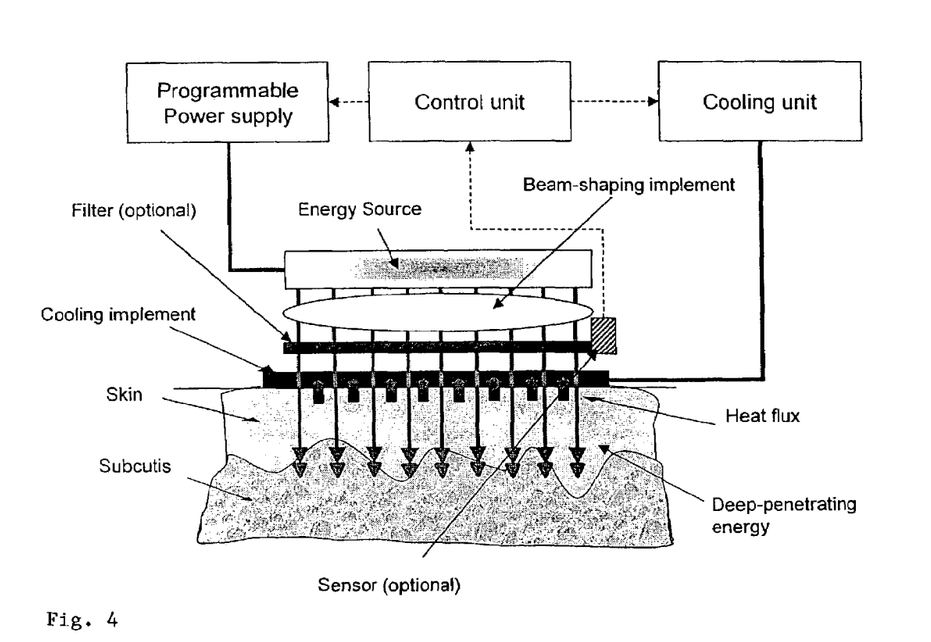
FIG. 4 is a schematic diagram of apparatus suitable for practicing the teachings of this invention.

Apparatus for implementing the technical concept is illustrated by FIG. 4. This implementation is exemplary, and a suitable configuration can be easily derived by those skilled in the art for particular applications. The cooling unit can be a thermoelectric element, an enclosure with cooling agent, a stream of cold gas (or liquid) or other cooling unit known in the art. Phase-changing materials can also be used for cooling. Preferably, skin surface temperature during the cooling phase should be maintained within the range between 0 C and 25 C. Preferable tissue temperature on the heating phase is in the range between 25 C and 45 C. In one embodiment of the invention, optical radiation is used on the heating phase of the cycle. In this embodiment, the energy source can be a laser, an LED, a lamp (discharge, halogen or other), or a combination or an array thereof. The spectral composition of the source can be either narrow- or broadband, with the range of wavelengths between 400 nm and 2000 nm. Spectral filtration can be used for further modifying spectral composition of the beam in order to achieve optimal penetration. The wavelengths used for a particular application will depend on the target tissue, the depth of the tissue and other factors. The light source is operated preferably in the continuous wave (CW) mode, with a preferred irradiance at the skin surface in the range between 0.1 and 100 W/cm2. The thermal cycle is organized in such a way as to maximize efficacy of treatment. Typically, duration of the cooling phase can be between 10 sec and 30 min, whereas duration of the heating phase can be between 1 sec and 4 min. The apparatus of FIG. 4 also includes a power supply for the energy source, a suitable control unit, an optional sensor, the function of which will be discussed later, and other components normally used in such apparatus.

The invention can be practiced in two distinctive modes (See FIGS. 5 and 6): in the protective mode, thermal cycling is used to protect adjacent (typically, upper) tissue from unwanted damage; whereas in the therapeutic mode thermal cycling is used substantially as a treatment modality.

Figure 5:
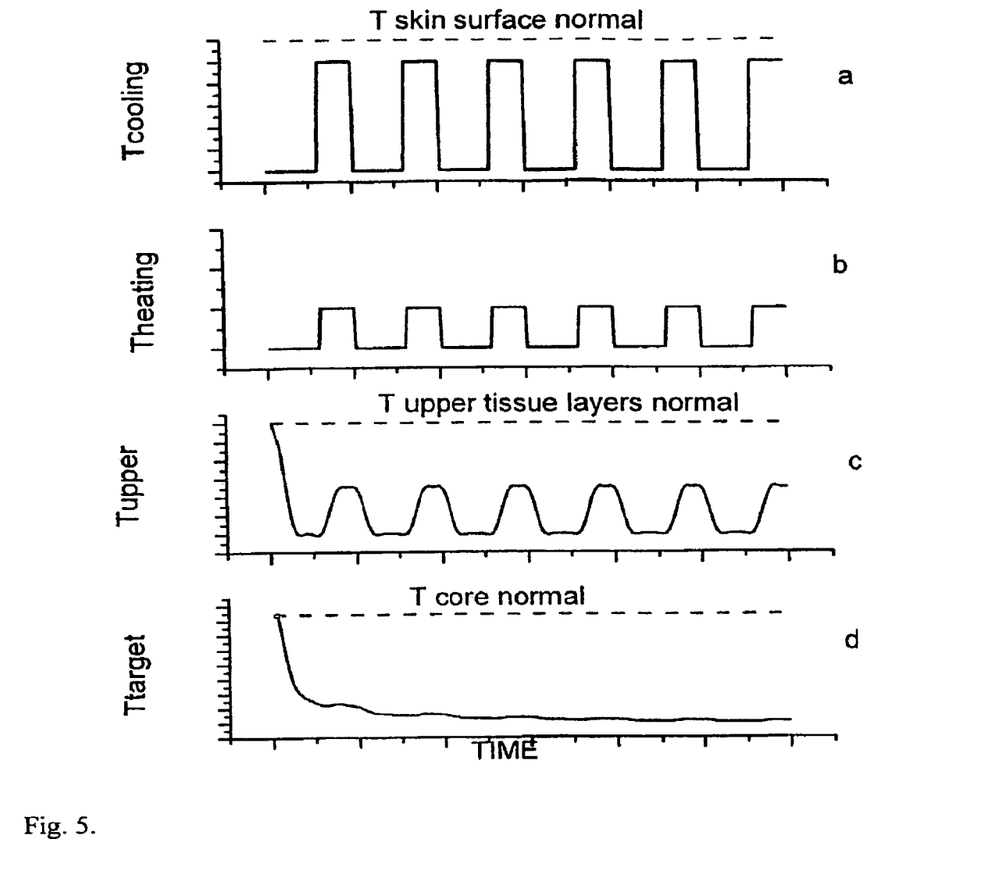
FIGS. 5a-5d are diagrams illustrating cooling temperature (T cooling), heating temperature (T heating), temperature in an upper layer of the skin (T upper) and target temperature at depth (T target) relative to normal core body temperature (T core normal) for successive cooling/heating cycles in a protective mode.
Figure 6:
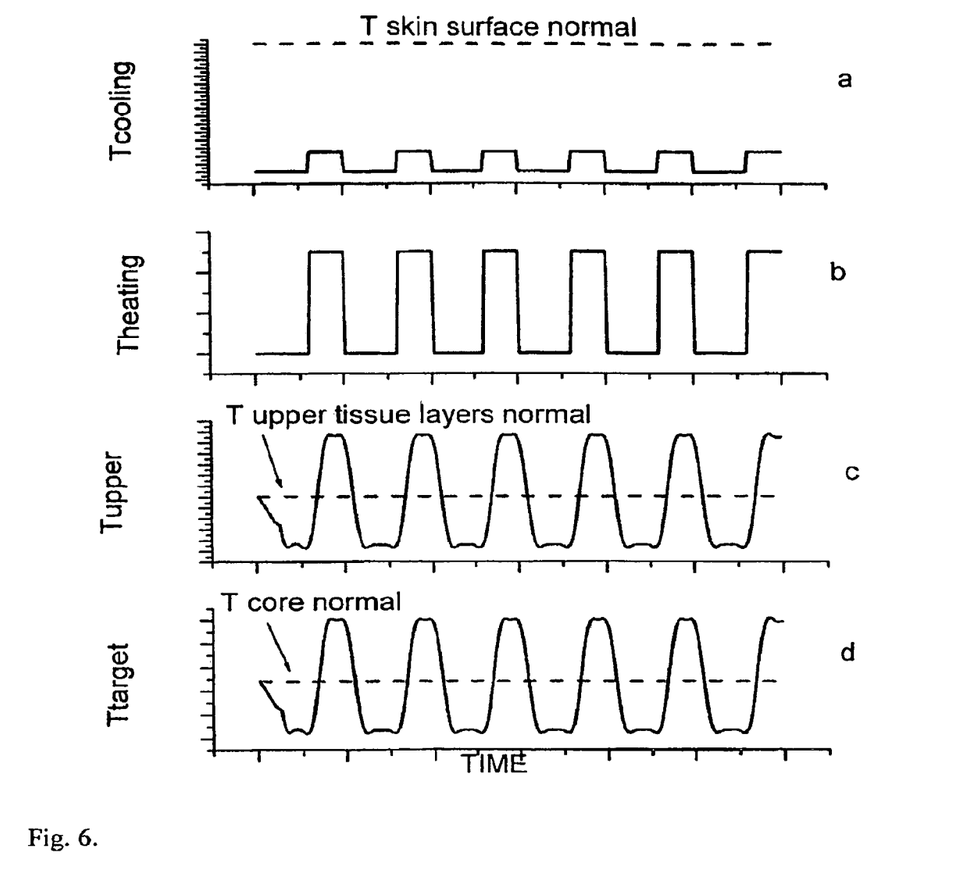
FIG. 6a-6d are diagrams illustrating cooling temperature (T cooling), heating temperature (T heating), temperature in an upper layer of the skin (T upper) and target temperature at depth (T target) relative to normal core body temperature (T core normal) for successive cooling/heating cycles in a therapeutic mode.

The invention can be practiced in at least two distinct modes (See FIGS. 5 and 6). In the protective mode of FIG. 5, initially applied cooling rapidly lowers the temperature at the skin surface, the target region and all tissue therebetween. Before the patient experiences pain or discomfort, and before thermal damage occurs outside the target region, a heating phase is initiated. The radiation from the energy source is sufficient to raise the temperature at the skin surface and below to a depth above the treatment region to a temperature above a discomfort or damage temperature, but has little effect on the treatment region at depth. This results in the temperature of the treatment region continuing to drop slightly with successive cooling cycles. This mode of thermal cycling is thus used to protect adjacent (typically, upper) tissue from unwanted damage. In the therapeutic mode shown in FIG. 6, thermal cycling is used substantially as a treatment modality. Here, the cooling and radiation parameters are selected so that, during heating cycles, the temperature at both the surface and the treatment region rise above normal body temperature, the treatment region thus being cycled between cold therapy and heat therapy. While in FIG. 6, the target region is heated above normal body temperature during heating portions of each cycle, this is not a limitation on the invention, and cyclically heating the target region to a selected temperature below normal body temperature may also have therapeutic effect for some conditions. Cycling may also be practiced by heating the target region to a temperature sufficient to cause hyperthermia, for example 42 to 47° C., either with or without simultaneous cooling to protect overlying tissue, and then either reducing or removing the radiation or increasing cooling to cool the treatment region below normal body temperature, this being done cyclically.

Figure 7:
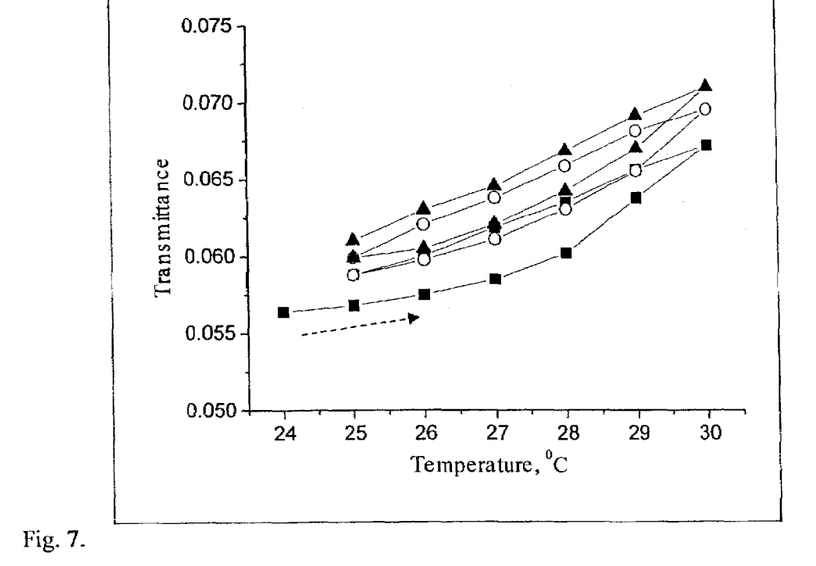
FIG. 7 is a diagram illustrating the hysterisis of optical transmittance in fat.

Thermal cycling offers another advantage when optical radiation is used as the deep-penetrating energy. Specifically, it has been demonstrated with optical measurements, that the rate of increase in optical transmittance when fresh human fatty tissue is heated exceeds the rate of decrease in optical transmittance when the same tissue is cooled (See FIG. 7). There is an indication of accumulated irreversible structural change in the fatty tissue caused by thermal cycling in relatively narrow temperature ranges between 25 and 30 C. As a consequence, the penetration depth of the optical radiation (and the efficiency of the heating phase) can be augmented by multiple cycling.

In some embodiments, the applicator (handpiece) of the apparatus can be realized as a stationary implement, which is placed on the treatment area prior to initiating thermal cycling.

Figure 8:
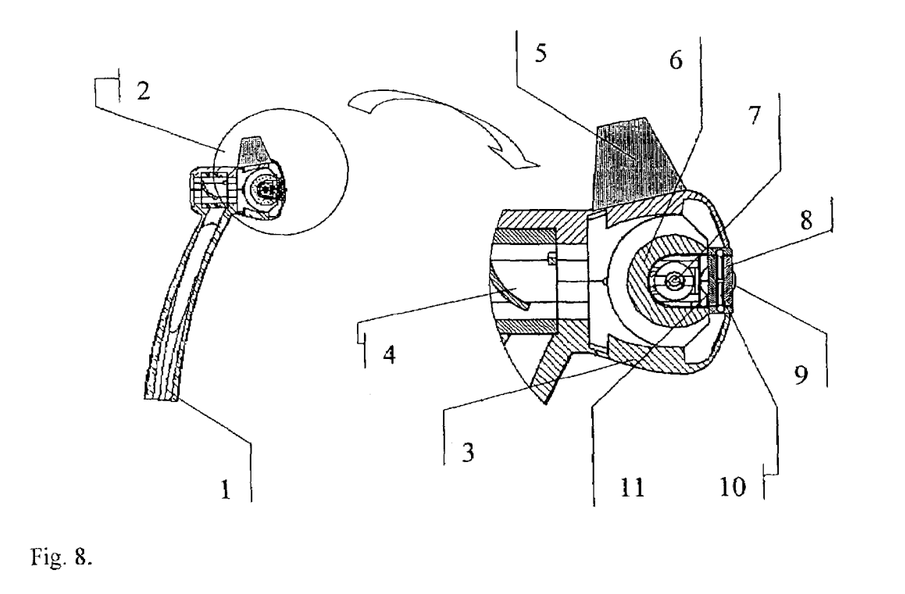

In other embodiments, the handpiece can be manually or mechanically scanned along the skin surface (See FIG. 8). Thermal cycling can be performed concurrently with scanning. Alternatively, thermal cycling can be implemented by performing at least one (preferably, several) passes on the cooling phase, followed by at least one (preferably, several) passes on the heating phase, and repeating the cycle until desired treatment effect is achieved. Referring to FIG. 8a, an exemplary scanning handpiece is shown which includes a handle 1 and an applicator 2. Referring to FIG. 8b, the applicator 2 includes a mount 3, a reflector cooling fan 4, an optional pressure or acoustic generator, vibrator ormassaging implement 5, a reflector 6, a radiation source (an arc or halogen lamp for the embodiment shown) 7, a cooling plate 8, an optional wheel 9 functioning as a mechanical velocity sensor, a cooling agent 10 and an optical filter 11.

Figure 9:
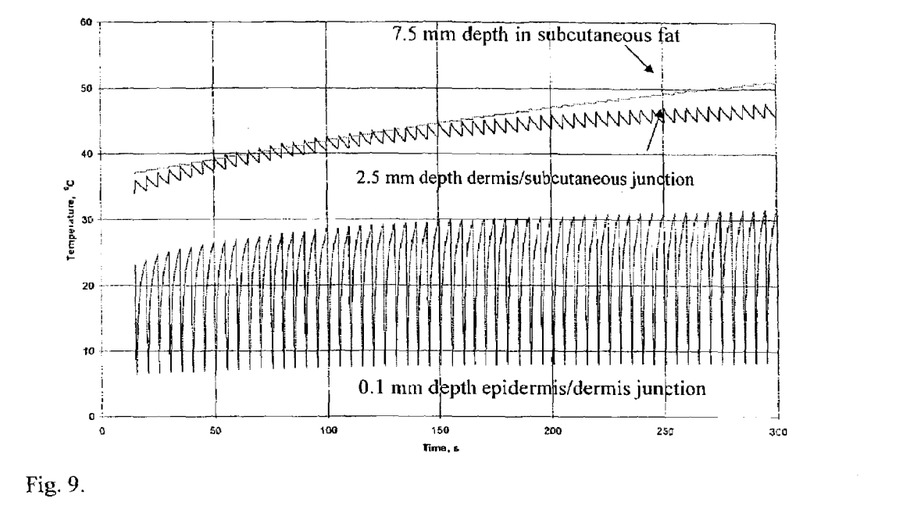
FIG. 9 is a diagram illustrating temperature dynamics at different depth in the skin when in multi-scan mode using non-selective heating with the applicator shown in FIG. 8.

The apparatus of FIG. 8 can be used, in particular, in a multi-scan mode. The multi-scan mode results in non-uniform cycling of temperature at different depths. FIG. 9 shows temperature at the epidermis/dermis junction (0.1 mm depth), dermis/hypodermis junction (2.5 mm depth) and subcutaneous fat (7.5 mm depth) as a function of time for multi-scan operation. Calculations have been done for the following conditions: wavelength 800-1800 nm (filtered spectrum of halogen lamp), power density 80 W/cm2, width of optical beam across scanning direction is 1 cm, speed of scan is 10 cm/s, length of scan is 50 cm, temperature of cold sapphire window in contact with the skin is −10° C. For scanning mode, the temperature of the contact plate can be significantly lower than the skin freezing temperature and at fast scanning speeds (about 10 cm/s), can be as low as −50° C. without risk of cold injury. FIG. 9 shows that the amplitude of thermal oscillations decreases with depth in skin. However, the time of stabilization of the temperature for deep targets can be long: 0.1 mm-100 s or 10 scans, 2.5 mm-5 min or 30 scans, 7.5 mm-15 min or 90 scans.

Figure 10:
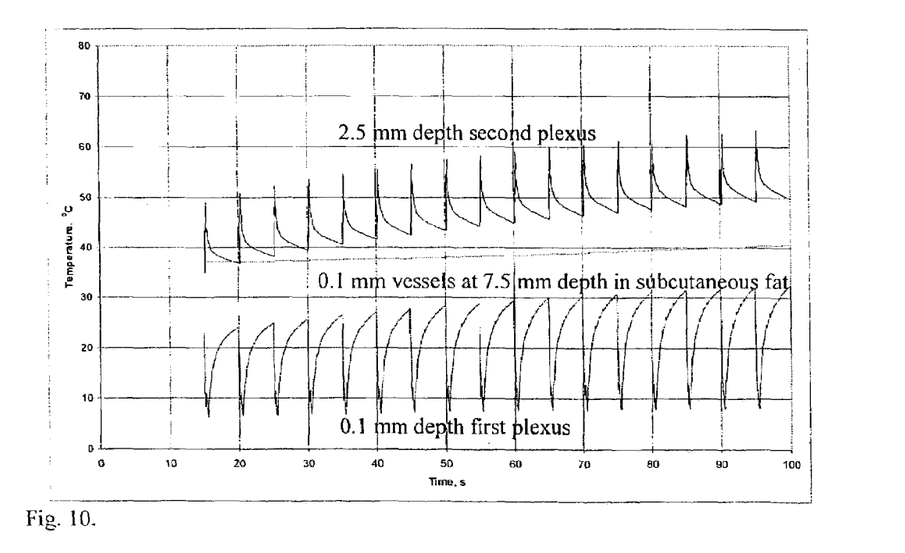
FIG. 10 is a diagram illustrating temperature dynamics in blood vessels at different depths in the skin in multi-scan mode using non-selective heating with the applicator shown in FIG. 8.

FIG. 10 shows temperatures at the blood vessels in first plexus (0.015 mm diameter, 0.1 mm depth), second plexus (0.2 mm diameter, 2.5 mm depth), and subcutaneous fat (0.1 mm diameter, 7.5 mm depth) as a function of time for multi-scan operation. Calculations have been done for the following conditions: wavelength 400-1800 nm (filtered spectrum of halogen lamp), power density 65 W/cm2, width of optical beam across scanning direction is 1 cm, speed of scan is 10 cm/s, length of scan is 50 cm, temperature of cold sapphire window in contact with the skin is −10° C. FIG. 10 shows that the amplitude of thermal oscillations in blood vessels is significant in the skin and negligible in the subcutaneous fat. Large temperature oscillations at the vessels in the second plexus (up to 10° C.) can-be effective for treatment of various conditions at the deep dermis and dermis/hypodermis junction and for improvement of cosmetic appearance of cellulite. Since the temperature of vessels in the subcutaneous fat is continuously rising, this treatment can be effective for increasing the rate of lypolysis.

Where energy source is a continuous wave (CW) or other long duration source, the apparatus or device for various of the embodiments may be slid or scanned over the surface of the patient's skin to overlie successive treatment regions, the dwell time, and thus the treatment duration, for each such region being a function of the rate at which the device is moved. The device may be moved over each treatment region multiple times during a single treatment. Since the device will typically also include a skin cooling mechanism, concurrent heating and cooling is effected for each region as the device passes thereover. The device may also include a cooling mechanism ahead of the portion of the device under the energy source to pre-cool skin above the treatment region (see for example issued U.S. Pat. Nos. 6,273,884 and 6,511,475, which are incorporated herein by reference). The power density $P_s$ for this sliding mode of operation is:

$$P_S = P_0 T v/d,$$

Were $P_0$ is power density for the organ/region being treated in a stationary mode V is speed of sliding, d is spot or aperture size in the direction of scanning, T is interval between two consecutive passes through same spot.

Treatment time is $$T_S = T_0 T v/d,$$

where $T_0$ is the stationary mode treatment time for the organ/region being treated In order for the multiple passes to be beneficial, T should be less than the thermal relaxation time of the tissue being treated in the region at depth. However, when in either stationary mode or sliding mode, the treatment time can be greater than the thermal relaxation time of the tissue being treated.

Any of the embodiments can include a contact sensor to assure good optical and thermal coupling, and systems operating in the sliding mode may also include one or more motion sensors to control radiation delivery, cooling and other functions dependent on scanning speed, to enhance system safety and for other reasons.

In addition to coupling the deep heating treatment of this invention with deep cooling to enhance treatment of fat, bone, muscle, etc., the applicator may also include a massager, vibrator or other mechanical stimulation device, an ultrasonic or other acoustic stimulator or a DC or other suitable electrical stimulation source. It has been found that such mechanical or electrical stimulation is more effective when tissue temperature deviates from normal body temperature (ie., for hot or cold tissue). Similarly, the effect of deep heating may be enhanced by massage or other stimulation because both heat and cold generally penetrates better in compressed skin and subdermal tissue. Thus, the combination of deep heating and mechanical or electrical stimulation may provide significantly better results then either one alone. Heating may also be enhanced by supplementing the optical heating with, for example electro-stimulation by AC/DC, or additional heating by RF, etc. Tensioning or pressure applied to the skin overlying the treatment region may also enhance treatment effect and decrease patient discomfort/pain sensation.

While an optical radiation source has been utilized for preferred embodiments, other forms of electromagnetic radiation such as microwave or radio frequency radiation can be used on the heating phase of the cycle. Alternatively, acoustic energy can be used. Unless otherwise indicated, the term radiation, as used herein, shall refer to the output from all such sources. The power of the source utilized should be selected in order to maintain the temperature of the targeted tissue within the preferred range.

The effectiveness of the invention may also be further increased by practicing a thermotolerance regimen. In this mode, the magnitude of temperature deviations from normal skin surface temperature which a patient can tolerate increases gradually from cycle to cycle, permitting treatment temperatures, and thus treatment effectiveness to also be gradually increased from cycle to cycle. This mode allows further increasing protection of cutaneous tissues from unwanted damage.

It may also be possible to correlate the period and phase of the thermal cycle with sub-circadian biological rhythms of the patient. Such combination can further optimize treatment results by using naturally occurring oscillations of biochemical activity in cutaneous and subcutaneous tissues. Furthermore, the temporal structure of the thermal cycling can deviate from simple harmonic oscillations and be comprised, for example, of several, or even an infinite number of harmonics.

In certain embodiments, the cooling implement can be realized as a layer (film, wrap) placed over the treatment region and the irradiating applicator can be realized as a head scanned on top of the cooling implement. Thermal cycling is achieved as a result of multiple passes of the irradiating applicator.

Some embodiments of the invention can incorporate a feedback loop between the applicator and the control unit. The feedback loop can incorporate a single or multiple sensors registering the state of the apparatus and the treatment area. For example, a thermal sensor can be used to initiate the heating phase of the cycle when tissue temperature drops below a certain threshold, and initiate the cooling phase of the cycle when the temperature exceeds another threshold. Other sensor types include, but are not limited to, scanning speed sensors, contact sensors, pressure sensors, skin detectors, and skin response sensors.

In some embodiments of the invention, an additional stimulating implement can be integrated into the applicator (see FIG. 8b). The purpose of the implement is to optimize tissue structure and facilitate thermal cycling. The implement can be, for example, mechanical (knitting, rolling, or pulling action) or vacuum (negative/positive pressure in the treatment area). Other forms of tissue stimulation may also be utilized, for example, ultrasonic or other acoustic stimulation, or electrical stimulation.

While several embodiments of the invention have been described and illustrated herein, those of ordinary skill in the art will readily envision a variety of other means and structures for performing the functions and/or obtaining the results and/or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention. In the claims, all transitional phrases or phrases of inclusion, such as "comprising," "including," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively.

What is claimed is:

1. A method for treating at least a selected target region at depth of a patient's body while protecting non-targeted tissue comprising:
    (a) cooling the patient's skin surface to a temperature below normal body temperature for a selected duration;
    (b) selectively applying radiation to the patient's skin above said region at least one of before, during and after step (a); and
    (c) repeating at least one of steps (a) and (b) for a selected number of cycles, the temperature to which the patient's skin surface is cooled and said duration being sufficient to cool said region to a selected temperature below normal body temperature during at least cooling portions of cycles, wherein said region is at or below the border zone of the dermis and hypodermis.

2. A method as claimed in claim 1 wherein said selected duration is at least about 10 seconds.

3. A method as claimed in claim 2 wherein said selected duration is between approximately 10 seconds and 30 minutes.

4. A method as claimed in claim 1 wherein step (b) is performed after step (a) and has a duration of from approximately 1 second to 4 minutes.

5. A method as claimed in claim 1 wherein step (a) is performed continuously and step (b) is performed at intervals during step (a).

6. A method as claimed in claim 1 wherein said selected region is subcutaneous fat, and wherein said selected temperature is low enough to result in at least a selective phase change of at least a portion of said fat.

7. A method as claimed in claim 6 wherein said radiation is of sufficient power and duration and of appropriate wavelength to heat said region to at least a temperature where the phase of the fat cells is altered.

8. A method as claimed in claim 1 and wherein said radiation is of sufficient power and duration and of appropriate wavelength to heat said region to at least a temperature where at least one of the biophysical and biochemical characteristics of cells in the selected region is altered.

9. A method as claimed in claim 1 wherein said radiation is of sufficient power and duration and of appropriate wavelength to heat tissue above said selected region to protect said tissue, but not to significantly heat said region.

10. A method as claimed in claim 1 wherein said treatment involves cycling cooling and heating of said region, step (b) being performed after step (a), and said radiation being of sufficient power and duration and of appropriate wavelength to heat said region to an appropriate temperature to effect said treatment.

11. A method as claimed in claim 1 including detecting a selected condition of the patient during at least one of steps (a) and (b), and utilizing said detecting step to control at least one of steps (a) and (b).

12. A method as claimed in claim 1 including stimulating said selected region during at least one of before, during and after at least one of steps (a) and (b).

13. A method as claimed in claim 12 wherein said stimulating is performed at least one of mechanically, acoustically and electrically.

14. A method as claimed in claim 1 wherein at least one of the period and phase of cycles of steps (a) and (b) are correlated with a sub-circadian biological rhythm of the patient.

15. A method as claimed in claim 1 wherein said radiation is from a continuous wave (CW) source and cooling is also performed from a substantially continuously operating source, and wherein step (a) is performed by passing an applicator outputting said cooling source over the patient's skin overlying said selected region at a selected rate, and step (b) is performed by passing an applicator outputting said radiation over the patient's skin overlying said selected region at a selected rate.

16. A method as claimed in claim 15 wherein the same applicator is used to perform both steps (a) and (b).

17. A method as claimed in claim 16 wherein steps (a) and (b) are performed during the same passes of the applicator over the patient's skin.

18. A method for treating at least a selected target region at depth of a patient's body while protecting non-targeted tissue comprising:
    (a) cooling the patient's skin surface to a temperature below normal body temperature for a selected duration; wherein step (a) is performed by passing an applicator outputting said cooling over the patient's skin overlying said selected region at a selected rate,
    (b) selectively applying radiation to the patient's skin above said region at least one of before, during and after step (a); wherein step (b) is performed by passing an applicator outputting said radiation over the patient's skin overlying said selected region at a selected rate, radiation power is increased by a factor of T v/d over the power required for a stationary applicator, where T is the interval between passes over the same region, v is the rate of movement of the applicator and d is applicator aperature size; and (c) repeating at least one of steps (a) and (b) for a selected number of cycles, the temperature to which the patient's skin surface is cooled and said duration being sufficient to cool said region to a selected temperature below normal body temperature during at least cooling portions of cycles, wherein said radiation is from a continuous wave (CW) source and cooling is also performed from a substantially continuously operating source.

19. A method as claimed in claim 18 wherein treatment time where the applicator is passed over the patient's skin is also increased by a factor of T v/d.

20. A method as claimed in claim 18 wherein T is less then the thermal relaxation time of tissue in said selected region.

21. Apparatus for treating at least a selected target region at depth of a patient's body while protecting non-targeted tissue comprising:

a mechanism for cooling the patient's skin surface to a temperature below normal body temperature for a selected duration;

a mechanism for selectively applying radiation to the patient's skin above said region at least one of before, during and after the cooling of the patient's skin surface; and controls for causing at least one of the mechanism for cooling and the mechanism for applying radiation to be operated for a selected number of cycles, and for controlling the temperature to which the patient's skin surface is cooled and said duration to sufficiently cool said region to a selected temperature below normal body temperature during at least cooling portions of cycles, wherein said region is at or below the border zone of the dermis and hypodermis.

22. Apparatus as claimed in claim 21 wherein said selected duration is at least about 10 seconds.

23. Apparatus as claimed in claim 22 wherein said selected duration is between approximately 10 seconds and 30 minutes.

24. Apparatus as claimed in claim 21 wherein said mechanism for applying radiation is operated after said mechanism for cooling and the applied radiation has a duration of from approximately 1 second to 4 minutes.

25. Apparatus as claimed in claim 21 wherein said mechanism for cooling is operated continuously and said mechanism for applying radiation is operated at intervals during the operation of the mechanism for cooling.

26. Apparatus as claimed in claim 21 wherein said selected region is subcutaneous fat, and wherein said selected temperature is low enough to result in at least a selective phase change of at least a portion of said fat.

27. Apparatus as claimed in claim 26 wherein said radiation is of sufficient power and duration and of appropriate wavelength to heat said region to at least a temperature where the phase of the fat cells is altered.

28. Apparatus as claimed in claim 21 wherein said radiation is of sufficient power and duration and of appropriate wavelength to heat said region to at least a temperature where at least one of the biophysical and biochemical characteristics of cells in said selected region is altered.

29. Apparatus as claimed in claim 21 wherein said radiation is of sufficient power and duration and of appropriate wavelength to heat tissue above said selected region to protect said tissue, but not to significantly heat said region.

30. Apparatus as claimed in claim 21 wherein said treatment involves cycling cooling and heating of said region, said mechanism for applying radiation being operated after said mechanism for cooling, and said radiation being of sufficient power and duration and of appropriate wavelength to heat said region to an appropriate temperature to effect said treatment.

31. Apparatus as claimed in claim 21 including a mechanism for detecting a selected condition of the patient during operation of at least one of said mechanisms, said controls utilizing the output from said mechanism for detecting to control at least one of the mechanism for cooling and the mechanism for applying radiation.

32. Apparatus as claimed in claim 21 including a stimulator stimulating said selected region during at least one of before, during and after operation of at least one of said mechanisms.

33. Apparatus as claimed in claim 32 wherein said stimulator is at least one of a mechanical, acoustical and electrical stimulator.

34. Apparatus as claimed in claim 21 wherein said mechanism for applying radiation includes a continuous wave (CW) source and said mechanism for cooling also operates substantially continuously, an applicator outputting said CW source passing over the patient's skin overlying said selected region at a selected rate, and an applicator for said cooling mechanism passing over the patient's skin overlying said selected region at a selected rate.

35. Apparatus as claimed in claim 34 wherein the same applicator is used for both said cooling and said radiation applying mechanisms.

36. Apparatus as claimed in claim 35 wherein said cooling and said radiation applying mechanisms are operated during the same passes of the applicator over the patient's skin.

37. Apparatus for treating at least a selected target region at depth of a patient's body while protecting non-targeted tissue comprising:

a mechanism for cooling the patient's skin surface to a temperature below normal body temperature for a selected duration;

a mechanism for selectively applying radiation to the patient's skin above said region at least one of before, during and after the cooling of the patient's skin surface, wherein said mechanism for applying radiation includes a continuous wave (CW) source and said mechanism for cooling also operates substantially continuously, an applicator outputting said CW source passing over the patient's skin overlying said selected region at a selected rate, and an applicator for said cooling mechanism passing over the patient's skin overlying said selected region at a selected rate.; and controls for causing at least one of the mechanism for cooling and the mechanism for applying radiation to be operated for a selected number of cycles, the temperature to which the patient's skin surface is cooled and said duration being sufficient to cool said region to a selected temperature below normal body temperature during at least cooling portions of cycles, wherein when the radiation applying mechanism is operated with the applicator being passed over the patient's skin, radiation power is increased by a factor of T v/d over the power required for a stationary applicator, where T is the interval between passes over the same region, v is the rate of movement of the applicator and d is applicator aperature size.

38. Apparatus as claimed in claim 37 wherein treatment time where the applicator is passed over the patient's skin is also increased by a factor of T v/d.

39. Apparatus as claimed in claim 37 wherein T is less then the thermal relaxation time of tissue in said selected region.

40. A method for treating at least a selected region at depth of a patient's body while protecting tissue above the selected region, comprising:
   (a) selectively delivering radiation to the patient's body above said selected region to heat said region;
   (b) concurrently cooling patient tissue above said selected region to a temperature below that of the selected region; and
   (c) cooling said region to a temperature below that of normal body temperature at least one of before and after heating of the region, there being at least one cycle of heating and cooling for said region, wherein said region is at or below the border zone of the dermis and hypodermis.

41. A method as claimed in claim 40 including:(d)applying at least one of mechanical, acoustic and electrical stimulation to said region.

42. A method for treating at least a selected region at depth of a patient's body comprising:
   cyclically applying radiation and cooling to the surface of the patient's skin above the selected region through at least one applicator providing substantially continuous cooling and radiation output, which applicator is passed over the patient's skin over the region multiple times for each cooling and radiation cycle, such that said selected region is cooled to a selected temperature below normal body temperature for at least a portion of said application, wherein said region is at or below the border zone of the dermis and hypodermis.

43. A method as claimed in claim 42 wherein a single applicator simultaneously applies cooling and radiation as it is passed over the patient' skin.

44. A method as claimed in claim 42 wherein a single applicator successively applies cooling and radiation during cooling and radiation portions respectively of each cycle, the applicator making multiple passes over the patient's skin for at least one of said portions.

45. A method for treating at least a selected target region at depth of a patient's body while protecting non-targeted tissue comprising:
   (a) cooling the patient's skin surface to a temperature below normal body temperature for a selected duration;
   (b) selectively applying radiation to the patient's skin above said region after step (a), said radiation being of sufficient power and duration and of appropriate wavelength to heat said region to an appropriate temperature to, in conjunction with step (a), effect said treatment; and
   (c) repeating at least one of steps (a) and (b) for a selected number of cycles, the temperature to which the patient's skin surface is cooled and said duration being sufficient to cool said region to a selected temperature below normal body temperature during at least cooling portions of cycles, wherein said region is at or below the border zone of the dermis and hypodermis.

46. A method for treating at least a selected target region at depth of a patient's body while protecting non-targeted tissue comprising:
   (a) passing an applicator outputting a substantially continuously operating cooling source over the patient's skin overlying said selected region at a selected rate to cool the patient's skin surface to a temperature below normal body temperature for a selected duration;
   (b) passing an applicator outputting radiation from a substantially continuous wave radiation source over the patient's skin overlying said selected region at a selected rate to selectively applying radiation to said region at least one of before, during and after step (a); and
   (c) repeating at least one of steps (a) and (b) for a selected number of cycles, the temperature to which the patient's skin surface is cooled and said duration being sufficient to cool said region to a selected temperature below normal body temperature during at least cooling portions of cycles, wherein said region is at or below the border zone of the dermis and hypodermis.

47. A method as claimed in claim 46 wherein the same applicator is used to perform both steps (a) and (b).

48. A method as claimed in claim 47 wherein steps (a) and (b) are performed during the same passes of the applicator over the patient's skin.

* * * * *